United States Patent
Zhang et al.

(10) Patent No.: US 10,775,278 B2
(45) Date of Patent: Sep. 15, 2020

(54) SCRUBBING AND SAMPLING DEVICE, CARD READER APPARATUS AND GATE APPARATUS

(71) Applicants: Tsinghua University, Haidian District, Beijing (CN); Nuctech Company Limited, Haidian District, Beijing (CN)

(72) Inventors: Qingjun Zhang, Beijing (CN); Yuanjing Li, Beijing (CN); Ziran Zhao, Beijing (CN); Ge Li, Beijing (CN); Qiufeng Ma, Beijing (CN)

(73) Assignees: Tsinghua University, Haidian District, Beijing (CN); NUCTECH COMPANY LIMITED, Haidian District, Beijing (CN)

( * ) Notice: Subject to any disclaimer, the term of this patent is extended or adjusted under 35 U.S.C. 154(b) by 281 days.

(21) Appl. No.: 15/826,098

(22) Filed: Nov. 29, 2017

(65) Prior Publication Data

US 2018/0164194 A1    Jun. 14, 2018

(30) Foreign Application Priority Data

Dec. 8, 2016 (CN) .......................... 2016 1 1127319

(51) Int. Cl.
*G01N 1/22* (2006.01)
*G06K 13/08* (2006.01)
*G01N 33/00* (2006.01)
*G01N 1/02* (2006.01)

(52) U.S. Cl.
CPC .......... *G01N 1/2205* (2013.01); *G01N 33/00* (2013.01); *G06K 13/08* (2013.01); *G01N 2001/022* (2013.01); *G01N 2001/028* (2013.01)

(58) Field of Classification Search
CPC ....... G01N 2001/022–028; G01N 1/22; G01N 1/44; G01N 33/021; G01N 33/0036–0057; G01N 33/0021
USPC ............ 73/23.2, 28.01, 31.07, 31.05, 864.71
See application file for complete search history.

(56) References Cited

U.S. PATENT DOCUMENTS

| | | | |
|---|---|---|---|
| 6,874,685 B1 * | 4/2005 | Moreau .............. | G06Q 20/3437 235/384 |
| 7,116,798 B1 * | 10/2006 | Chawla .............. | G01N 33/0057 382/100 |
| 2003/0106362 A1 * | 6/2003 | Megerle .................. | G01N 1/22 73/23.2 |

(Continued)

FOREIGN PATENT DOCUMENTS

DE    102007051492 A1 *  4/2009  ............... G01N 1/02

*Primary Examiner* — Alexander A Mercado
(74) *Attorney, Agent, or Firm* — Merchant & Gould P.C.

(57) ABSTRACT

It is disclosed a scrubbing and sampling device, a card reader apparatus and a gate apparatus. The scrubbing and sampling device includes: a scrubbing and sampling portion including a first wheel and a second wheel, which are respectively capable of rotating around respective rotating axes, and a scrubbing conveyor belt tensioned by the first wheel and the second wheel and driven by rotation of the first wheel and the second wheel, to move between them; and an desorbing portion configured to desorb properties of an sample that is conveyed into the desorbing portion. The scrubbing conveyor belt is configured to move through the desorbing portion such that the desorbing portion desorbs the sample on the scrubbing conveyor belt when the scrubbing conveyor belt enters the desorbing portion.

11 Claims, 1 Drawing Sheet

(56) References Cited

U.S. PATENT DOCUMENTS

| | | | |
|---|---|---|---|
| 2006/0042407 A1* | 3/2006 | Napoli | G01N 27/622 |
| | | | 73/863.12 |
| 2007/0086925 A1* | 4/2007 | O'Donnell | G01N 1/2214 |
| | | | 422/82.05 |
| 2008/0217524 A1* | 9/2008 | Mawer | G01N 1/02 |
| | | | 250/281 |
| 2008/0264186 A1* | 10/2008 | Nacson | G01N 1/02 |
| | | | 73/863.12 |
| 2009/0044641 A1* | 2/2009 | Konduri | G01N 1/2273 |
| | | | 73/863.11 |
| 2010/0126284 A1* | 5/2010 | Boudries | G01N 1/405 |
| | | | 73/863.12 |
| 2014/0345364 A1* | 11/2014 | Lin | G01N 27/622 |
| | | | 73/28.01 |

* cited by examiner

SCRUBBING AND SAMPLING DEVICE, CARD READER APPARATUS AND GATE APPARATUS

CROSS-REFERENCE TO RELATED APPLICATION

The present application claims priority to Chinese Patent Application No. 201611127319.6, filed on Dec. 8, 2016, entitled "SCRUBBING AND SAMPLING DEVICE, CARD READER APPARATUS AND GATE APPARATUS", which is incorporated herein by reference in its entirety.

TECHNICAL FIELD

Embodiments of the present disclosure relate to technical field of analysis and inspection, and particularly to a scrubbing and sampling device, a card reader apparatus and a gate apparatus.

BACKGROUND

In order to prevent terror and drug smuggling, some technologies of inspection on trace drug or exploder are developed. Thus, it is needed to provide a device that may effectively and rapidly perform sampling on a card or a certificate, so as to complete the inspection.

SUMMARY

According to an aspect of the present disclosure, there is provided a scrubbing and sampling device including:

a scrubbing and sampling portion comprising a first wheel and a second wheel, which are respectively capable of rotating around respective rotating axes, and a scrubbing conveyor belt tensioned by the first wheel and the second wheel and driven, by rotation of the first wheel and the second wheel, to move between them; and.

an desorbing portion configured to desorb properties of a sample that is conveyed into the desorbing portion by the scrubbing conveyor belt, wherein the scrubbing conveyor belt is configured to move through the desorbing portion such that the desorbing portion can desorb the sample on the scrubbing conveyor belt when the scrubbing conveyor belt enters the desorbing portion.

In an embodiment, the scrubbing and sampling portion includes an object intake such that an object to be inspected can be inserted into and then brought out of the scrubbing and sampling portion through the object intake.

In an embodiment, the scrubbing and sampling portion includes a sample chamber configured to receive the objected to be inspected, such that the scrubbing conveyor belt contacts a surface of the object to be inspected received in the sample chamber and scrubs the surface of the object to be inspected when the scrubbing conveyor belt moving so as to capture the sample on the surface of the object to be inspected.

In an embodiment, the desorbing portion includes a desorbing chamber including a scrubbing conveyor belt intake through which the scrubbing conveyor belt enters the desorbing chamber, a scrubbing conveyor belt exit through which the scrubbing conveyor belt exits the desorbing chamber and a sample outlet configured to output the sample in the desorbing chamber.

In an embodiment, the desorbing portion includes a temperature controlling device configured to control internal temperature of the desorbing portion to be at a desire temperature range, and the temperature controlling device includes a heating device configured in the desorbing chamber, a temperature sensor configured to measure the internal temperature and a thermal insulating layer configured to insulate heat inside the desorbing chamber from ambient.

In an embodiment, the desorbing chamber includes a scrubbing conveyor belt exit sealant configured at the scrubbing conveyor belt exit to seal the scrubbing conveyor belt exit and clean the scrubbing conveyor belt passing through the scrubbing conveyor belt exit.

In an embodiment, the scrubbing and sampling device includes a housing in which the scrubbing and sampling portion and the desorbing portion are received and by which the scrubbing and sampling portion and the desorbing portion are insulated from external circumstance, and the scrubbing and sampling device further includes a gas filtering device in the housing which is configured to filter and clean the gas within the housing.

In an embodiment, the object intake is configured to allow the object to be inspected to be inserted into the object intake in a direction of movement of the scrubbing conveyor belt or in a direction perpendicular to the direction of the movement of the scrubbing conveyor belt.

In an embodiment, the object to be inspected includes a card or a certificate.

In an embodiment, the scrubbing conveyor belt exit sealant includes a corrugated liner or bush.

According to an aspect of the present disclosure, there is provided a card reader apparatus, used for reading a card, wherein the card reader apparatus includes the above described scrubbing and sampling device, the card reader apparatus is configured to, when the card is placed in the card reader apparatus, read the card, and at the same time, or posteriorly, or before that, scrub a surface of the card to capture sample on the surface of the card.

In an embodiment, the scrubbing and sampling portion includes a card reading chamber in which the card is placed, and, before or after or at the time when the card reader apparatus reads the card, the scrubbing conveyor belt contacts the surface of the card placed in the card reader chamber and scrubs the surface to capture the sample on the surface upon its movement.

According to an aspect of the present disclosure, there is provided a gate apparatus including the above described card reading apparatus.

BRIEF DESCRIPTION OF THE DRAWINGS

Figure 1:
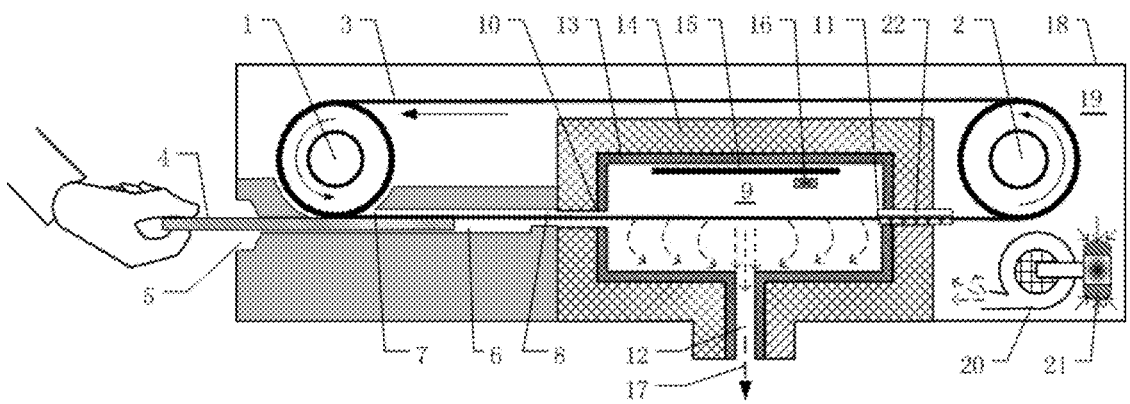
FIG. 1 is a schematic view of a scrubbing and sampling device according to an embodiment of the present disclosure.

Although there are various changeable and replaceable formations of the embodiment of the invention, some specific embodiments are illustrated exemplarily in the drawings and described in the text in detail. However, it is appreciated that the attached drawings and the detailed description are not intended to limit the present invention to the disclosed embodiments, instead of, to cover all modifications, equivalents and replacements that fall into the inspirits and scope of the present invention defined by the claims. The drawings are provided for illustrating and are not protracted in scale.

In the present disclosure, the terms of "first" and "second" do not mean difference in the aspect of order or importance, instead, they are only provided for distinguishing different components.

Embodiments of the present disclosure are described with reference to the drawings.

Embodiments of the present disclosure provide a scrubbing and sampling device including: a scrubbing and sampling portion including a first wheel 1 and a second wheel 2, which are respectively capable of rotating around respective rotating axes, and a scrubbing conveyor belt 3 tensioned by the first wheel and the second wheel and driven by rotation of the first wheel and the second wheel, to move between them; and an desorbing portion configured to desorb properties of an sample that is conveyed into the desorbing portion. The scrubbing conveyor belt moves through the desorbing portion such that the desorbing portion can desorb the sample on the scrubbing conveyor belt when the scrubbing conveyor belt enters the desorbing portion. The scrubbing and sampling device according to the embodiment of the present disclosure, due to its automatic scrubbing and sampling, is more suitable for sampling semi-volatile material and particles material effectively than a device that is configured to sample by directly sucking gas, and may effectively reduce technical requirement on detection device in terms of minimum detection limit, increase detection sensitivity and thus is more suitable for detecting whether a drug or exploder is carried during security inspection.

In embodiments of the present disclosure, the scrubbing and sampling portion includes an object intake 5 through which the object to be inspected 4 may be inserted into the scrubbing and sampling portion and then be drawn out of the scrubbing and sampling portion.

In an embodiment of the present disclosure, the scrubbing and sampling portion may include a sample chamber 6 configured to receive the object to be inspected 4. With this configuration, the scrubbing conveyor belt 3 may contact the surface of the object to be inspected 4 in the sample chamber 6, so as to scrub the sample on the surface of the object to be inspected 4 when the scrubbing conveyor belt 3 moving, so as to capture the sample on the surface of the object to be inspected 3. In an embodiment, the sample chamber 6 may be a card chamber.

Figure 2:
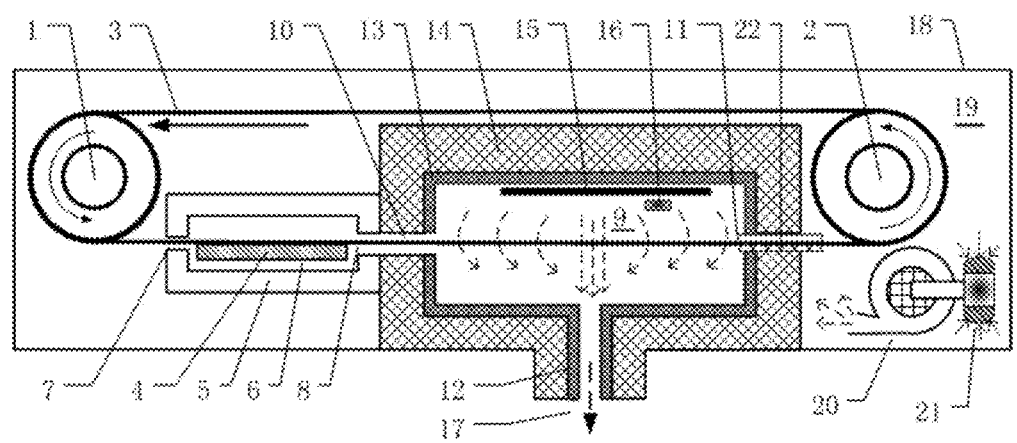
FIG. 2 is a schematic view of a scrubbing and sampling device according to another embodiment of the present disclosure.

In an embodiment of the present disclosure, the desorbing portion includes a desorbing chamber 9 that includes a scrubbing conveyor belt intake 10 through which the scrubbing conveyor belt enters the desorbing chamber, a scrubbing conveyor belt exit 11 through which the scrubbing conveyor belt exits from the desorbing chamber and a sample outlet 12 configured to output the sample in the desorbing chamber. In the scrubbing and sampling device as shown in FIG. 1 and FIG. 2, the sample outlet 12 is arranged at a bottom side of the scrubbing and sampling device. However, in other embodiments of the present disclosure, the sample outlet 12 may be arranged at a top side opposite to the bottom side of the scrubbing and sampling device, or a side of thereof that is between the top side and bottom side and different from or the same as the scrubbing conveyor belt intake 10 and scrubbing conveyor belt exit 11.

In an embodiment of the present disclosure, the desorbing portion includes a temperature controlling device configured to control internal temperature of the desorbing portion to be at a desired temperature range, and the temperature controlling device includes a heating device 15 arranged in the desorbing chamber, a temperature sensor 16 configured to measure the internal temperature and a thermal insulating layer 14 configured to insulate heat inside the desorbing chamber 9. In order that the scrubbed sample in the desorbing chamber 9 is rapidly evaporated and desorbed, the temperature controlling device is provided in the analyzing chamber 9. The temperature in the analyzing chamber 9 may be controlled by a computer in a range, such as, from 120° C. to 180° C. so as to sufficiently desorb the sample from the scrubbing conveyor belt. In the scrubbing and sampling device as shown in FIG. 1 and FIG. 2, the heating device 15 is arranged in an upper portion inside the desorbing chamber 9. In other embodiments of the present disclosure, the heating device 15 is arranged in a lower portion inside the desorbing chamber 9, that is, located below the scrubbing conveyor belt. The heating device 15 may include a plurality of heating elements, or may be a heating film that may heat the desorbing chamber 9 by irradiation.

In an embodiment of the present disclosure, the desorbing chamber 9 includes a scrubbing conveyor belt exit sealant configured at the scrubbing conveyor belt exit to seal the scrubbing conveyor belt exit and clean the scrubbing conveyor belt passing through the scrubbing conveyor belt exit.

In an embodiment of the present disclosure, in order to avoid interruption of ambient air, the scrubbing and sampling device includes a housing 18 in which the scrubbing and sampling portion and the desorbing portion are received and by which they are insulated from external circumstance, and the scrubbing and sampling device further includes a pump 20 located in the housing and configured to draw out gas within the housing. The scrubbing and sampling device further includes a gas filtering device 21 in the housing which is configured to filter and clean the gas within the housing. The pump 20 and the gas filtering device 21 in FIGS. 1 and 2 are merely intended to illustrate that they are provided in the housing without any definition of a connection and configuration of them in practice, which may be configured by those skilled in the art as required. In an embodiment of the present disclosure, the object 4 to be inspected may be a card or a credentials or a certificate.

Embodiments of the present disclosure further provide a card reader apparatus for reading a card information, wherein the card reader apparatus includes the above described scrubbing and sampling device, the card reader apparatus is configured to, when the card is placed in the scrubbing and sampling portion of the card reader apparatus, read the card, and at the same time, or posteriorly, or before that, scrub a surface of the card to capture the sample on the surface of the card by the scrubbing and sampling device. The device according to the embodiment of the disclosure has a compact and simple structure and may be implemented in a gate to automatically sample a card or a credentials or a certificate without opening a baggage or interrupting human body, so as to achieve trace substances inspection, thereby avoiding interruption to human body in a conventional security inspection.

In the embodiment, the scrubbing and sampling portion includes a card reader chamber 6 in which the card is placed. The card reader apparatus may read information of the card 4, and at the same time or posteriorly, the scrubbing conveyor strap 3 contacts the surface of the card 4 placed in the card reader chamber and scrubs the surface to capture the sample on the surface during its movement.

FIG. 1 and FIG. 2 are respectively schematic views of two embodiments of the scrubbing and sampling device. A difference between the two embodiments is in that, in the embodiment as shown in FIG. 1, a direction in which the card chamber intake 5 is oriented is parallel to a movement direction of the scrubbing conveyor belt 3, while in the embodiment as shown in FIG. 2, the direction in which the card chamber intake 5 is oriented is perpendicular to a movement direction of the scrubbing conveyor belt 3. Except the above configuration, the two embodiments are the same as each other in other aspects. For brief, the common features of the two embodiments are described in the following content and they both fall into scope of the present disclosure.

As shown in FIGS. 1 and 2, the scrubbing and sampling device according to embodiments of the present disclosure may include: a scrubbing and sampling portion, which includes a first wheel 1, a second wheel 2, a scrubbing conveyor belt 3, and an analyzing chamber 9. The scrubbing and sampling device further include a card chamber 6 and FIG. 2 shows that the objected to be inspected such as a card is placed in the card chamber 6. The scrubbing and sampling device is enclosed by a working chamber 19. The working chamber 19 is defined by the housing 18. In other words, the entire scrubbing and sampling device may be enclosed by the housing 18.

In the embodiment, the scrubbing and sampling portion is configured to continuously scrub the object such as the card and convey it into the desorbing chamber 9 in which the temperature may be raised. The first wheel 1 and the second wheel 2 are spaced apart from each other by a distance and the scrubbing conveyor belt 3 may pass through the card chamber 6 and the desorbing chamber 9 and wrap on the first wheel 1 and the second wheel 2 to form a circle. The first wheel 1 and the second wheel 2 rotate to drive the scrubbing conveyor belt 3 to move to scrub the card 4 in the card chamber 6, so as to capture sample, and then the scrubbing conveyor belt is moved into the desorbing chamber 9 to desorb the sample. By this way, the scrubbing conveyor belt 3 is looped to achieve sampling circularly. The scrubbing conveyor belt 3 may be made of any material that has properties of a high-temperature (above 120° C.) resistance, good unreactiveness, good toughness and good scrubbing effect, and be designed in a width that is the same as a width of an identification card or similar to a width of a passport, thereby improving adaptability. However, it is appreciated that the width of the scrubbing conveyor belt 3 may be designed to be any values. A computer may be used to control a motor to drive the scrubbing conveyor belt 3 to move in instant velocity to continuously scrub for sampling, or a motor and a position sensor may be provided to drive the scrubbing conveyor belt 3 to scrub for sampling according to a time order when the card 4 is placed in the card chamber 6 and then enter the desorbing chamber 9 and be positioned there for desorbing the sample according to a time order. For example, after it enters the desorbing chamber 9, the scrubbing conveyor belt 3 may stop such that a portion or segment of the scrubbing conveyor belt 3 on which the sample is attached may stay in the desorbing chamber 9 for a second or several seconds.

The card chamber 6 is provided with a card chamber intake 5 through which the card 4 may be correctly inserted. The scrubbing conveyor belt 3 may enter the card chamber 6 through the scrubbing conveyor belt intake 7 and the scrubbing conveyor belt exit 8, and pass through the card chamber 6. In the embodiment, when the card 4 is inserted, the surface of the scrubbing conveyor belt 3 is parallel to and contacts the surface of the card 4 so as to achieve high-effectively scrubbing on the card 4 for sampling. The scrubbing conveyor belt 3 then passes through the card chamber 6 and completes sampling, and then enters the desorbing chamber 9.

In an embodiment, the wheel or the rotating axis closer to the card chamber intake may impose elastic pressure in a direction perpendicular to the surface of the card such that the wheel may press the surface of the card when a card with different thicknesses is inserted into the card chamber intake and then the scrubbing conveyor belt may be in close contact with the card, so as to automatically scrub the surface when moving and pick up sample on the surface of the card.

The desorbing chamber 9 is provided with a scrubbing conveyor belt intake 10, a scrubbing conveyor belt exit 11 and a sample outlet 12. The scrubbing conveyor belt exit 8 of the card chamber 6 is adjacent to and communicated with the scrubbing conveyor belt intake 10 of the desorbing chamber. The scrubbing conveyor belt exit 11 may be provided with a corrugated flexible jacket 22, which on one hand, may seal the desorbing chamber 9 to certain extent to prevent the desorbed sample from leaking, and on the other hand, may clean the scrubbing conveyor belt 3. The corrugated flexible jacket 22 may be made of material, such as fluororubber, that is non-volatile and can work at high temperature.

The desorbing chamber 9 may be further provided with a heating device 15, a temperature sensor 16, and a thermal insulating case 14, which constitute a temperature controlling device and can ensure the desorbing chamber 9 to be at a desired temperature by control of a computer such that the sample may be sufficiently desorbed. The desorbing chamber 9 may be further provided with a desorbing chamber inner case 13, which may be made of an unreactive and high-temperature resistant material, such as liner pipe made of polytef, ceramic, glass or quartz, or may be made of metal material coated gold. The thermal insulating case 14 may be made of silica aerogel or glass or ceramic wool with a thickness of 20 mm.

The sample that is desorbed in the desorbing chamber 9 is guided to other desorb apparatus 17 through the sample outlet 12. The other desorb apparatus 17 may be, such as tornado-type sample injector, pre-condensation device, a commonly used six-way valve injector, IMS, MS, GC or other devices, which will not be described in detail.

The housing 18 encloses the above components in the working chamber 19, avoiding interruption from ambient air. The housing 18 may be made of metal material. The pump 20 may be used to suck air within the chamber such that the air may be filtered by the gas filter 21 so as to circle and clean the gas within the housing 18.

An embodiment of the present disclosure provides a gate apparatus including the card reader apparatus according to embodiments of the present disclosure. The card reader apparatus will not be described repeatedly again herein.

The automatic-circulation scrubbing and sampling device according to embodiments of the present disclosure may be configured in a gate apparatus, which operates in the following process:

when a passenger passes through the gate apparatus, inserts a card 4 into the card chamber 6 and draws it out of the card chamber 6, the scrubbing conveyor belt 3 close to the card chamber 6 may automatically rapidly scrub the card 4 for sampling; subsequently, the sample that is scrubbed by the scrubbing conveyor belt 3 from the card 4 is conveyed to the desorbing chamber 9 and is desorbed momentarily in the desorbing chamber 9 at high temperature; the desorbed sample is then guided to other apparatus 17 that is connected with the sample outlet 12; the entire process of scrubbing, sampling and desorbing may be completed in such as 4 seconds by controlling the velocity of the movement of the scrubbing conveyor belt 3. The above process may be circulated, thereby achieving sampling the card one by one without affecting passing of the crowd.

The sampling schemes in the embodiments of the present disclosure integrally involves advantages of "high speed, circulation and automation" and may rapidly sample the passengers one by one, overcoming defects in conventional manual sampling schemes which are impossible to perform effectively and are merely performed in a manner of a spot check and increasing inspection efficiency. Thus, the sampling schemes in the embodiments of the present disclosure are suitable for a gate of airport, highway or railroad and also suitable for rapid in-scene inspection for entrance of conference, creating a new mode of trace substance entry inspection.

Although some embodiments of the present invention that implement its general concept have been illustrated and described, it is appreciated that the described embodiments may be modified without departing away from the principle and inspirits of the general inventive concept. The scope of the present disclosure is defined by the attached claims and their equivalent.

The invention claimed is:

1. A scrubbing and sampling device, comprising:
   a scrubbing and sampling portion comprising a first wheel and a second wheel, which are respectively capable of rotating around respective rotating axes, and a scrubbing conveyor belt tensioned by the first wheel and the second wheel, forming a loop between the first wheel and the second wheel and driven by rotation of the first wheel and the second wheel, to move between them; and
   a desorbing portion configured to desorb properties of a sample that is conveyed into the desorbing portion,
   wherein the scrubbing conveyor belt is configured to move through the desorbing portion such that the desorbing portion desorbs the sample on the scrubbing conveyor belt when the scrubbing conveyor belt enters the desorbing portion,
   wherein the desorbing portion comprises a desorbing chamber comprising a scrubbing conveyor belt intake through which the scrubbing conveyor belt enters the desorbing chamber, a scrubbing conveyor belt exit through which the scrubbing conveyor belt exits the desorbing chamber and a sample outlet configured to output the sample in the desorbing chamber, and
   wherein the desorbing chamber comprises a scrubbing conveyor belt exit sealant configured at the scrubbing conveyor belt exit to seal the scrubbing conveyor belt exit and clean the scrubbing conveyor belt passing through the scrubbing conveyor belt exit.

2. The scrubbing and sampling device according to claim 1, wherein the scrubbing and sampling portion comprises an object intake, such that an object, which is to be inspected, is allowed to be inserted into and then brought out of the scrubbing and sampling portion through the object intake.

3. The scrubbing and sampling device according to claim 2, wherein the object intake is configured to allow the object to be inspected to be inserted into the object intake in a direction of movement of the scrubbing conveyor belt or in a direction perpendicular to the direction of movement of the scrubbing conveyor belt.

4. The scrubbing and sampling device according to claim 1, wherein the scrubbing and sampling portion comprises a sample chamber configured to receive an object, which is to be inspected, such that the scrubbing conveyor belt contacts a surface of the object to be inspected received in the sample chamber and scrubs the surface of the object to be inspected when the scrubbing conveyor belt moves, so as to capture the sample on the surface of the object to be inspected.

5. The scrubbing and sampling device according to claim 1, wherein the desorbing portion comprises a temperature controlling device configured to control internal temperature of the desorbing portion to be at a desired temperature range, and the temperature controlling device comprises a heating device arranged in the desorbing chamber, a temperature sensor configured to measure the internal temperature and a thermal insulating layer configured to insulate heat inside the desorbing chamber from ambient.

6. The scrubbing and sampling device according to claim 1, wherein the scrubbing and sampling device comprises a housing in which the scrubbing and sampling portion and the desorbing portion are received and by which the scrubbing and sampling portion and the desorbing portion are insulated from external circumstance, and the scrubbing and sampling device further comprises a gas filtering device in the housing which is configured to filter and clean a gas within the housing.

7. The scrubbing and sampling device according to claim 1, wherein an object to be inspected comprises a card or a certificate.

8. The scrubbing and sampling device according to claim 1, wherein the scrubbing conveyor belt exit sealant comprises a corrugated flexible jacket.

9. A card reader apparatus for reading card information, wherein the card reader apparatus comprises the scrubbing and sampling device according to claim 1, wherein
   the card reader apparatus is configured to, when a card is placed in the card reader apparatus, read the card, and at the same time, or posteriorly, scrub a surface of the card to capture the sample on the surface of the card; or
   the card reader apparatus is configured to, when the card is placed in the card reader apparatus, scrub a surface of the card to capture sample on the surface of the card and then read the card.

10. The card reader apparatus according to claim 9, wherein the scrubbing and sampling portion comprises a card reading chamber in which the card is placed, and, before or after or at the time when the card reader apparatus reads the card, the scrubbing conveyor belt contacts the surface of the card placed in the card reader chamber and scrubs the surface to capture the sample on the surface upon a movement of the scrubbing conveyor belt.

11. A gate apparatus comprising the card reading apparatus according to claim 9, wherein the gate apparatus is configured to allow a passenger to pass through the gate apparatus.

* * * * *